US005610056A

United States Patent [19]

Nakahata

[11] Patent Number: 5,610,056
[45] Date of Patent: Mar. 11, 1997

[54] USE OF STEM CELL FACTOR INTERLEUKIN-6 AND SOLUBLE INTERLEUKIN-6 RECEPTOR TO INDUCE THE DEVELOPMENT OF HEMATOPOIETIC STEM CELLS

[75] Inventor: Tatsutoshi Nakahata, Tokyo, Japan

[73] Assignees: Amgen Inc., Thousand Oaks, Calif.; Tosoh Corporation, Tokyo, Japan

[21] Appl. No.: 340,559

[22] Filed: Nov. 16, 1994

[51] Int. Cl.$^6$ .............................. A01N 63/00; C12N 5/00; A61K 38/20
[52] U.S. Cl. .............................. 435/378; 424/93.7; 514/2; 435/384; 435/386
[58] Field of Search .......................... 435/240.2, 240.21, 435/240.3, 240.31; 424/93.7; 514/2

[56] References Cited

U.S. PATENT DOCUMENTS

| | | | |
|---|---|---|---|
| 5,004,681 | 4/1991 | Boyse et al. | 435/2 |
| 5,061,620 | 10/1991 | Tsukamoto et al. | 435/7.21 |
| 5,154,921 | 10/1992 | Sager et al. | 424/93 |
| 5,192,553 | 3/1993 | Boyse et al. | 424/529 |
| 5,199,942 | 4/1993 | Gillis | 604/4 |

FOREIGN PATENT DOCUMENTS 04139082  2/1991  European Pat. Off. .

OTHER PUBLICATIONS

Nichols et al., Exp. Cell Res. 215 (1):237–39 (Nov. 1994).
Yoshida et al. Mechanisms of Development, 45 (2):163–71 (1994).
Muench et al., Exp Hematol, 20:339–49 (1992).
Han, Hokkaido Igaku Zasshi (Japan), 67(5): 674–83 (Sep. 1992).
McNiece et al., Exp. Hematol., 19: 226–231 (1991).
Ho et al., Bone Marrow Transplant, 7 (Supp 1): 13–17 (1991).
Takaue et al., Blood, 76(2) 330–35 (1990).
Chang et al, The Lancet, p. 294 (Feb. 8, 1986).
Molineux et al., Blood, 76 (10):2153–58 (1990).
Robinson et al., Am. J. of the Medical Sciences, 300 (5):311–21 (1990).
Robinson et al., Am. J. of the Medical Sciences 300(4):237–44 (1990).
Iscove et al, J. of Immunology, 145 (1):190–195 (1990).
Terstappen et al., Leukemia, 6(10): 1001–10 (1992).
Schmitt et al, Genes & Development, 5:728–40 (1991).
Chang et al., Bone Marrow Transplantation, 4:5–9 (1989).
Iscove et al, J. of Immunology, 142:2332–37 (1989).
Ulich et al. Blood, 75 (1):48–53 (1990).
Berenson et al., Blood, 77:1717–22 (1991).
Henschler et al., Blood, 84(9):2898–03 1994.
Metcalf, PNAS (USA), 88: 11310–14 (1991).
Debili et al., Blood, 82(1):84–95 (1993).
Muira et al., Exp. Hematol., 21 (1):143–49 (1993).
Jacobsen et al, Exp. Hematol, 22 (11): 1064–69 (1994).
Zurerzina et al, Blood, 82 (10 Suppl 1):374(A) (1993).

Loury et al., Exp. Hematol., 20: 937–42 (1992).
Flanagan et al., "The kit Ligand: A Cell Surface Molecule Altered in Steel Mutant Fibroblasts", *Cell*, 63:185–194 (1990).
Hirata et al., "Characterization of IL–6 Receptor Expression by Monoclonal and Polyclonal Antibodies", *The Journal of Immunology*, 143:2900–2906 (1989).
Hondo et al. "Human Soluble IL–6 Receptor: Its Detection and Enhanced Release by HIV Infection", *The Journal of Immunology*, 148:2175–2180 (1992).
Hondo et al., "Quantitative Analysis of Serum IL–6 and Its Correlation with Increased Levels of Serum IL–2R in HIV–Induced Diseases", *The Journal of Immunology*, 145:4059–4064 (1990).
Imai et al., "Interleukin–6 Supports Human Megakaryocytic Proliferation and Differentiation In Vitro", *Blood*, 78(8):1969–1974 (1991).
Iscove et al., "Net Increase of Pluripotential Hematopoietic Precursors in Suspension Culture in Response to IL–1 and IL–3", *The Journal of Immunology*, 142:2332–2337 (1989).
Koike et al., "Synergism of BSF–2/Interleukin 6 and Interleukin 3 on Development of Multipotential Hemopoietic Progenitors in Serum–Free Culture", *J. Exp. Med.*, 168:879–890 (1988).
Koury and Bondurant, "Erythropoietin Retards DNA Breakdown and Prevents Programmed Death in Erythroid Progenitor Cells", *Science*, 248:378–381 (1990).
Krantz, S. B., "Erythropoietin", *Blood*, 77(3):419–434 (1991).
Langley et al., "Soluble Stem Cell Factor in Human Serum", *Blood*, 81(3):656–660 (1993).
Liboi et al., "Erythropoietin Receptor Signals Both Proliferation and Erythroid–specific Differentiation", *Proc. Natl. Acad. Sci., USA*, 90:11351–11355 (1993).
Mayani and Lansdorp, "Thy–1 Expession Is Linked to Functional Properties of Primitive Hematopoietic Progenitor Cells from Human Umbilial Cord Blood", *Blood*, 83(9):2410–2417 (1994).
Nakahata and Ogawa, "Hemopoietic Colony–forming Cells in Umbilical Cord Blood with Extensive Capability to Generate Mono– and Multipotential Hemopoietic Progenitors", *J. Clin. Invest.*, 70:1324–1328 (1982).
Nishi et al., "Induction of Mixed Erythroid–Megakaryocyte Colonies and Bipotential Blast Cell Colonies by Recombinant Human Erythropoietin in Serum–Free Culture", *Blood*, 76(7):1330–1335 (1990).
Okumura et al., "Changes in Cell Surface Antigen Expressions During Proliferation and Differentiation of Human Erythroid Progenitors", *Blood*, 80(3):642–650 (1992).

(List continued on next page.)

*Primary Examiner*—Chhaya D. Sayala
*Assistant Examiner*—Jhung-Won Colby
*Attorney, Agent, or Firm*—Craig A. Crandall; Daniel R. Curry; Steven M. Odre

[57] ABSTRACT

Stem cell factor in combination with interleukin-6 and soluble interleukin-6 receptor supports proliferation, differentiation and terminal maturation of erythroid cells from normal human hematopoietic stem cells.

6 Claims, 8 Drawing Sheets

OTHER PUBLICATIONS

Saito et al., "Preparation of Monoclonal Antibodies Against the IL-6 Signal Transducer, gp130, That can Inhibit IL-6-Mediated Functions", *Journal of Immunological Methods*, 163:217–223 (1993).

Suzuki et al., "Serum Soluble Interleukin-6 Receptor in MRL/lpr Mice is Elevated with Age and Mediates the Interleukin-6 Signal", *Eur. J. Immunol.*, 23:1078–1082 (1993).

Taga et al., "Functional Inhibition of Hematopoietic and Neurotrophic Cytokines by Blocking the Interleukin 6 Signal Transducer gp130", *Proc. Natl. Acad. Sci. USA*, 89:10998–11001 (1992).

Taga et al., "Interleukin-6 Triggers the Association of Its Receptor with a Possible Signal Transducer, gp130", *Cell*, 58:573–581 (1989).

Yasukawa et al., "Purification and Characterization of Soluble Human IL-6 Receptor Expressed in CHO Cells", *J. Biochem.*, 108:673–676 (1990).

Yin et al., "Involvement of IL-6 Signal Transducer gp130 in IL-11-Mediated Signal Transduction", *The Journal of Immunology*, 151(5):2555–2561 (1993).

Yu et al., "Apoptosis and Hematopoiesis in Murine Fetal Liver", *Blood*, 81(2):373–384 (1993).

Zsebo et al., "Stem Cell Factor is Encoded at the SI Locus of the Mouse and Is the Ligand for the c-kit Tyrosine Kinase Receptor", *Cell*, 63:213–224 (1990).

| Culture time | Day 7 | | | Day 14 | | | Day 21 | | |
|---|---|---|---|---|---|---|---|---|---|
| Cell number (x10³) | Total cell | E-blast | Erythrocyte | Total cell | E-blast | Erythrocyte | Total cell | E-blast | Erythrocyte |
| Il-6 | 0.9 | 0 | 0 | 0 | 0 | 0 | 0 | 0 | 0 |
| sIL-6R | 0.6 | 0 | 0 | 0 | 0 | 0 | 0 | 0 | 0 |
| IL-6+sIL-6r | 1.9 | 0 | 0 | 0 | 0 | 0 | 0 | 0 | 0 |
| SCF | 5.5 | 0 | 0 | 1.7 | 0 | 0 | 4.4 | 0 | 0 |
| SCF+IL-6 | 11.7 | 0 | 0 | 43.8 | 0 | 0 | 15.0 | 0 | 0 |
| SCF-IL-6+sIL-6R | 75.8 | 28.7 | 0 | 1062.0 | 640.0 | 201.8 | 4346.0 | 2859.6 | 126.1 |
| EPO | 16.6 | 16.6 | 0 | 215.0 | 200.2 | 14.9 | 18.8 | 11.8 | 7.0 |
| EPO+IL6 | 16.6 | 16.6 | 0 | 230.0 | 212.1 | 17.9 | 20.0 | 9.2 | 10.8 |
| EPO+IL-6+sIL-6R | 19.7 | 19.2 | 0 | 230.0 | 220.1 | 9.9 | 56.3 | 53.8 | 1.8 |
| IL-3 | 5.0 | 0 | 0 | 18.1 | 0 | 0 | 3.8 | 0 | 0 |
| IL-3+IL-6 | 7.5 | 0 | 0 | 16.9 | 0 | 0 | 25.0 | 0 | 0 |
| IL-3+IL-6+sIL-6R | 10.0 | 0 | 0 | 50.0 | 23.2 | 0 | 50.0 | 25.3 | 0 |
| G-CSF | 2.5 | 0 | 0 | 4.4 | 0 | 0 | 5.0 | 0 | 0 |
| G+IL-6 | 2.2 | 0 | 0 | 5.6 | 0 | 0 | 5.0 | 0 | 0 |
| G+IL-6+sIL-6R | 2.2 | 0 | 0 | 3.1 | 0 | 0 | 1.3 | 0 | 0 |
| GM-CSF | 1.6 | 0 | 0 | 0.6 | 0 | 0 | 2.5 | 0 | 0 |
| GM+IL-6 | 1.6 | 0 | 0 | 3.8 | 0 | 0 | 3.8 | 0 | 0 |
| GM+IL-6+sIL-6R | 4.1 | 0.1 | 0 | 3.1 | 0.2 | 0 | 7.5 | 1 | 0 |

USE OF STEM CELL FACTOR INTERLEUKIN-6 AND SOLUBLE INTERLEUKIN-6 RECEPTOR TO INDUCE THE DEVELOPMENT OF HEMATOPOIETIC STEM CELLS

BACKGROUND OF THE INVENTION

1. Field of the Invention

The present invention relates to the use of stem cell factor in association with interleukin-6 and soluble interleukin-6 receptor to induce the development of hematopoietic stem cells. More particularly, the present invention involves the combined use of these factors to promote the production of erythroid cells.

2. Description of the Background

Interleukin-6 (IL-6) is a cytokine that appears to be one of the mediators of the response to viral and bacterial infections and to shock. The purification, cloning and use of IL-6 has been reported (EP 220 574, published May 6, 1987, Revel et al.; WO 88/00206, published Jan. 14, 1988, Clark et al.). It has also been reported that gp130, which is a second receptor molecule of IL-6 (as well as oncostatin M, ciliary neurotrophic factor and IL-11), is expressed on the surface of a wide variety of cells. In addition, an extracellular soluble form of the interleukin-6 receptor (sIL-6R) can associate, when occupied by IL-6, with membrane-anchored gp130 and thereby activate cellular signaling processes (8–10). The purification and cloning of soluble IL-6 receptor have been reported, as has its combined use with IL-6 in conditions such as bacterial infections, burns and trauma (EP 413 908, published Feb. 27, 1991, Novick et al.).

Stem cell factor (SCF) is an early acting hematopoietic factor. The purification, cloning and use of SCF have been reported (see PCT WO 91/05795, entitled "Stem Cell Factor"). The use of SCF has been described for enhancing engraftment of bone marrow and bone marrow recovery as well as for the treatment of leukopenia and thrombocytopenia. The use of SCF in combination with IL-6 has been described, but there are no previous reports of the combined use of SCF, IL-6 and soluble IL-6 receptor.

Erythropoiesis, the production of red blood cells, occurs continuously to offset cell destruction. Erythropoiesis is a precisely controlled physiological mechanism enabling sufficient numbers of red blood cells to be available for proper tissue oxygenation, but not so many that the cells would impede circulation. The formation of red blood cells occurs in the bone marrow and is under the control of the hormone, erythropoietin. It is generally accepted that erythropoietin is the primary humoral regulator of erythropoiesis and that it is the single factor which supports the proliferation and terminal maturation of erythroid cells from hematopoietic stem cells (1–4). Erythropoiesis has been extensively studied, and there have been no previous descriptions of the physiological regulation of erythropoiesis by a pathway other than erythropoietin signaling.

SUMMARY OF THE INVENTION

The present invention demonstrates that a combination of soluble IL-6 receptor (sIL-6R) and IL-6 together with stem cell factor (SCF) can support the proliferation, differentiation and terminal maturation of erythroid cells from purified human hematopoietic cells in the absence of erythropoietin (EPO). Neither sIL-6R or IL-6, when singly combined with SCF, demonstrates this effect in the absence of erythropoietin.

The present invention provides for the generation of erythroid cells from hematopoietic stem cells (e.g., $CD34^+$ cells) by means of a combination of sIL-6R, IL-6 and SCF. The effectiveness of the associated factors was also confirmed in serum-free cultures. A number of erythroid bursts and mixed erythroid colonies, containing a large number of mature erythroid cells, were developed from $CD34^+$ cells in methylcellulose culture with the combination of sIL-6R, IL-6 and SCF. The further addition of anti-gp130 monoclonal antibodies (MAbs) to the cultures completely abrogated the production of erythroid cells, whereas the addition of anti-erythropoietin antibody failed to affect the generation of erythroid cells from $CD34^+$ cells.

These results clearly demonstrate that mature erythroid cells can be produced from hematopoietic progenitors in the absence of erythropoietin. Together with previous reports that human sera contain detectable levels of sIL-6R, IL-6 and SCF (5–7), it is likely that normal erythropoiesis is regulated physiologically by two different pathways: erythropoietin-mediated signaling and a novel mechanism with gp130 in combination with SCF signaling.

DETAILED DESCRIPTION OF THE INVENTION

Figure 1:
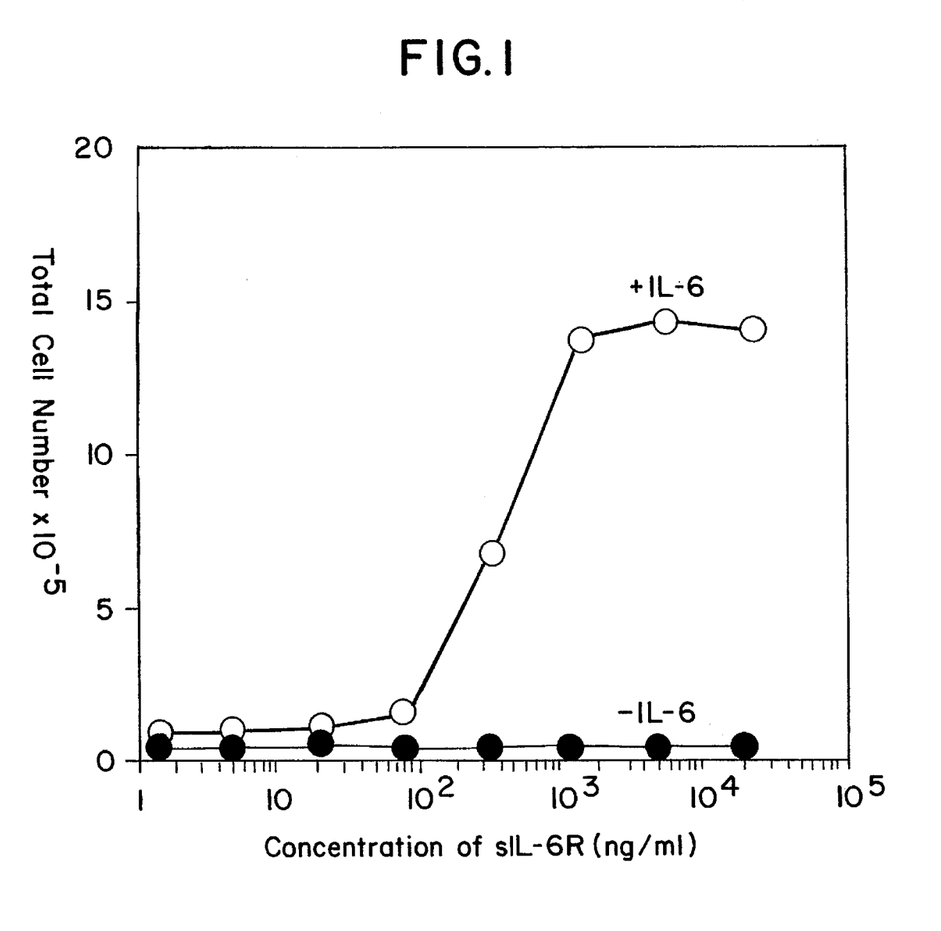
FIG. 1 illustrates the effects of varying amounts of sIL-6R in the presence of IL-6 and SCF.

The present invention was discovered during the study of the effects of gp130 signaling on human hematopoietic progenitor cells. Normal human hematopoietic stem cells were isolated from cord blood mononuclear cells and were cultured in the presence of varying concentrations of sIL-6R together with IL-6 and SCF. It was found that the total cell numbers increased in a dose-dependent manner. This increase was detectable with sIL-6R at a concentration as low as 80 ng/ml and appeared to plateau at 1280 ng/ml. FIG. 1 depicts the results of one experiment using varying amounts of sIL-6R in the presence of IL-6 and SCF.

The analyses of total cell numbers indicated more than 30-fold, 650-fold and 900-fold expansions of total cells in cultures at 7, 14 and 21 days of incubation, respectively, at the sIL-6R concentrations exceeding 1280 ng/ml. In the absence of IL-6, however, sIL-6R failed to increase the total cell number. These results clearly indicated that sIL-6R is functional and capable of transducing proliferative signals in CD34+ cells only in combination with IL-6.

Figure 2:
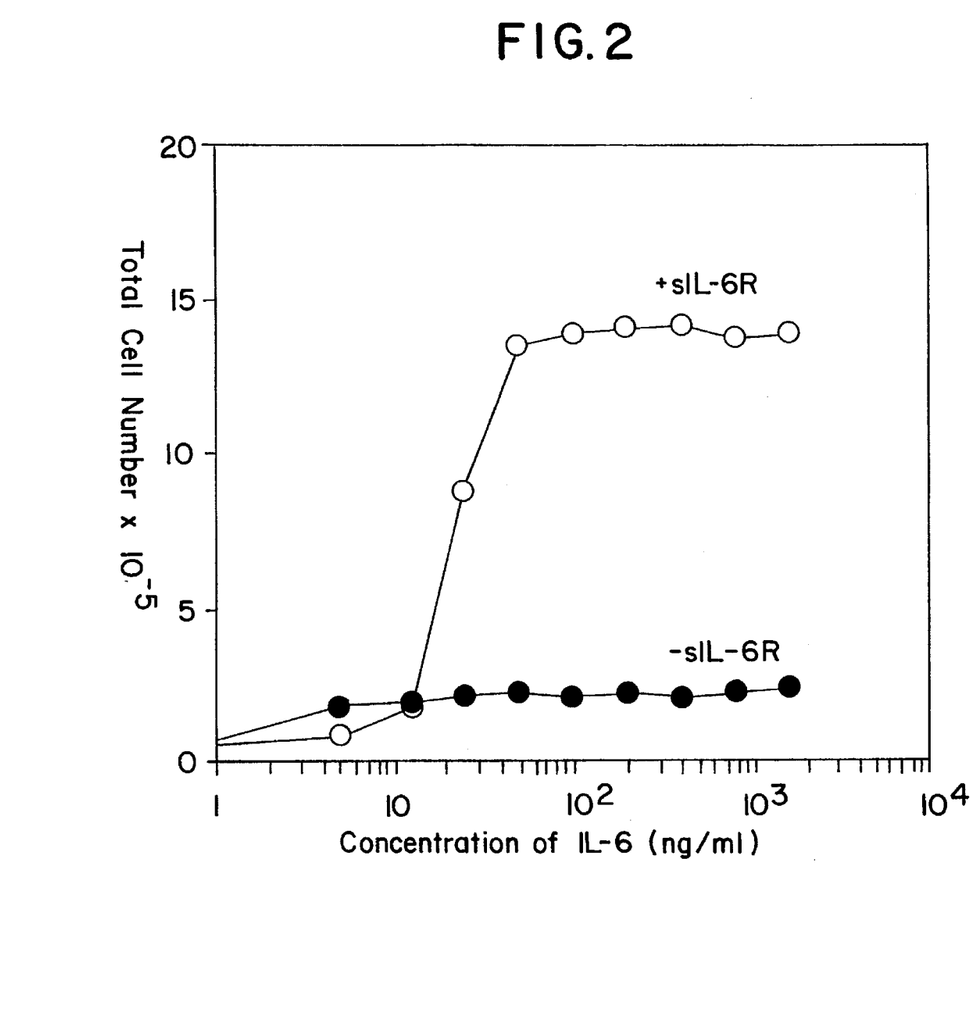
FIG. 2 the effects of varying amounts of IL-6 in the presence of sIL-6R and SCF.

Dose response studies of IL-6 also indicated a dose-dependent increase in the total cell numbers. A maximal cell number was obtained using IL-6 concentrations of 50–100 ng/ml in the presence of 1280 ng/ml sIL-6R (FIG. 2). In the absence of sIL-6R, however, IL-6 generated only a small increase in the number of total cells, even when used in amounts greater than 50 ng/ml. These results suggest that sIL-6R at 1280 ng/ml and IL-6 at 50 ng/ml may be an effective combination for the expansion of total cells from purified stem cells in serum-containing culture with SCF. The expansion of total cells by the combination of sIL-6R, IL-6 and SCF was also observed when CD34+ cells purified from human bone marrow were used (data not shown).

Figure 3:
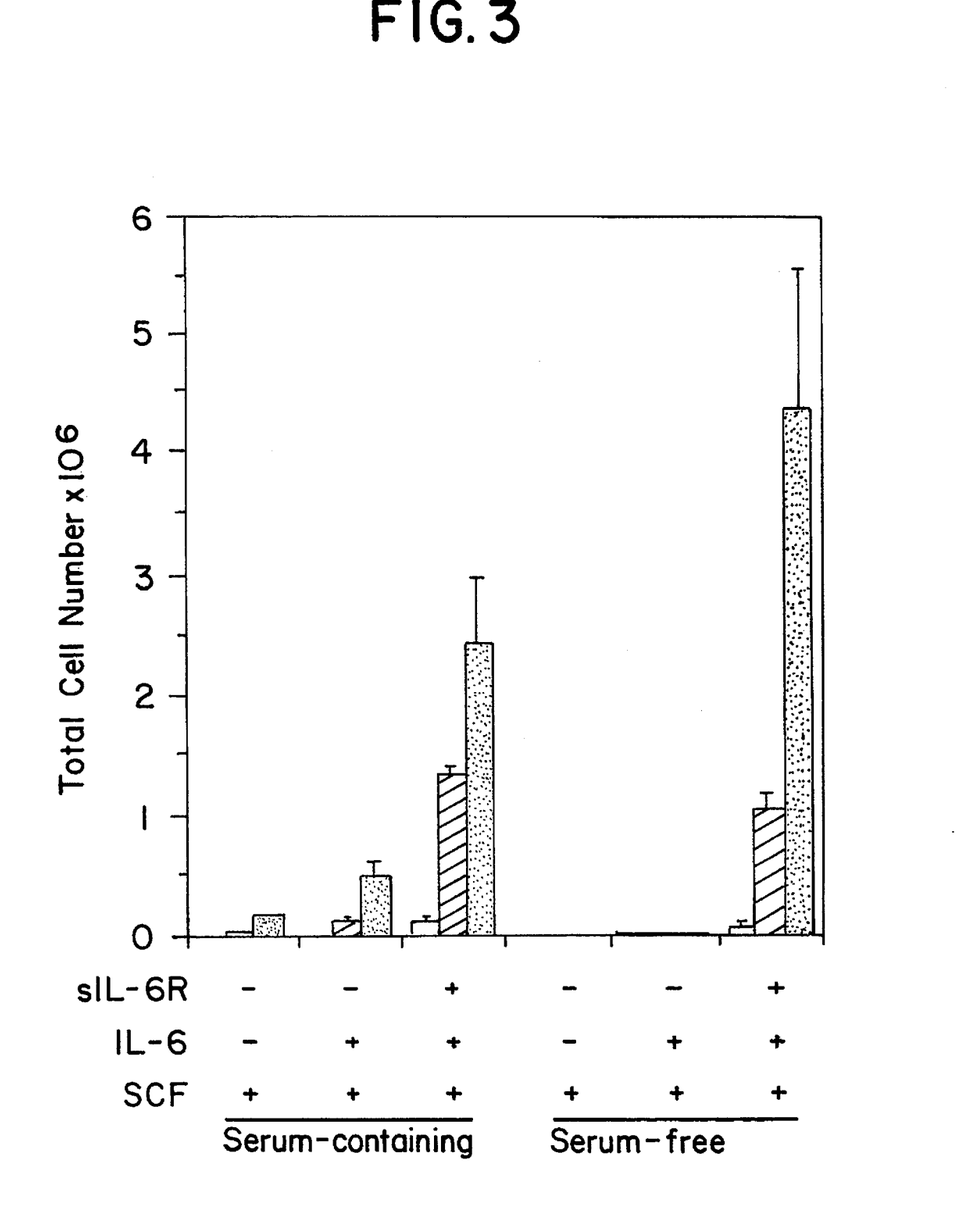
FIG. 3 illustrates the effects of SCF, IL-6/SCF and sIL-6R/IL-6/SCF on serum-free and serum-containing cultures.

It was possible that the observed effects of combined sIL-6R/IL-6 in serum-containing culture were due to the actions of these factors in conjunction with unknown factor(s) contaminating the fetal bovine serum (FBS), rather than to the sIL-6R/IL-6/SCF combination alone. To exclude this possibility, a serum-free suspension culture of CD34+ cord blood cells was studied. Surprisingly, an even greater synergy between sIL-6R, IL-6 and SCF, was observed in the serum-free cultures as compared to the serum-containing cultures (FIG. 3). Serum-free culture of cells with the combination of sIL-6R, IL-6 and SCF promoted 38-fold, 530-fold and 2200-fold expansions of total cell numbers at 7, 14 and 21 days of culture, respectively. Cells cultured in SCF alone, or in combination with IL-6, demonstrated only a 2.2 or 71.5-fold expansion even at day 21. These results clearly excluded the possible influence of unknown factors and demonstrated that sIL-6R in the presence of SCF does induce the expansion of hematopoietic stem cells.

Figure 4A:
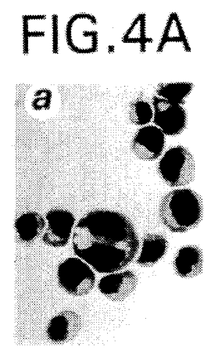
FIG. 4 depicts the nature of the generated erythroid cells.
Figure 4B:
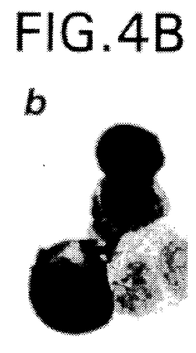
Figure 4C:
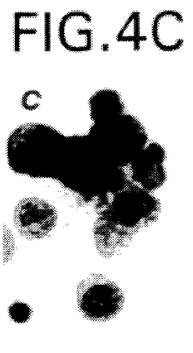
Figure 4D:
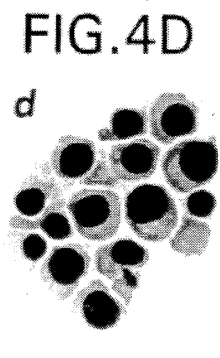

Cytocentrifuge preparations of expanded cells were stained with various cytochemical and immunological stains. Differential cell counts of these cells indicated the presence of mainly blast cells, such as those presented at day 7 of culture of CD34+ cord blood cells (FIG. 4a). Interestingly, a number of erythroblasts were observed in both serum-containing and serum-free suspension cultures, at day 14 of culture, when using the combination of sIL-6R, IL-6 and SCF. The nature of the erythroid cells was confirmed by benzidine-staining and immunostaining with monoclonal antibodies against glycophorin A (FIG. 4b) and hemoglobin-α (FIG. 4c). Some of the erythroid cells differentiated to the normoblast and enucleated erythrocyte stages (FIG. 4d). At 21 days of culture, most of the erythroid cells differentiated to the normoblast stage, and many enucleated erythrocytes were observed.

The absolute number of erythroid cells was calculated by total cell number and the occurrence of glycophorin A-positive cells on the cytospine slides. Weekly analyses of the absolute number of erythroid cells in serum-free cultures receiving various combinations of cytokines and sIL-6R are presented in FIG. 5.

The combination of sIL-6R, IL-6 and SCF stimulated the generation of not only total cell number but also total erythroid cells more significantly than did other combinations. At two weeks of culture, approximately 79% of the cells generated by the combination were erythroid cells (i.e., E-blasts and erythrocytes). At three weeks of culture, approximately 69% of the cells generated by the combination were erythroid cells. A small number of erythroid cells was also observed in cultures containing sIL-6R and IL-6 in combination with either IL-3 or GM-CSF, suggesting that gp130 signaling plays a role in the generation of erythroid cells in vitro.

Figure 5:
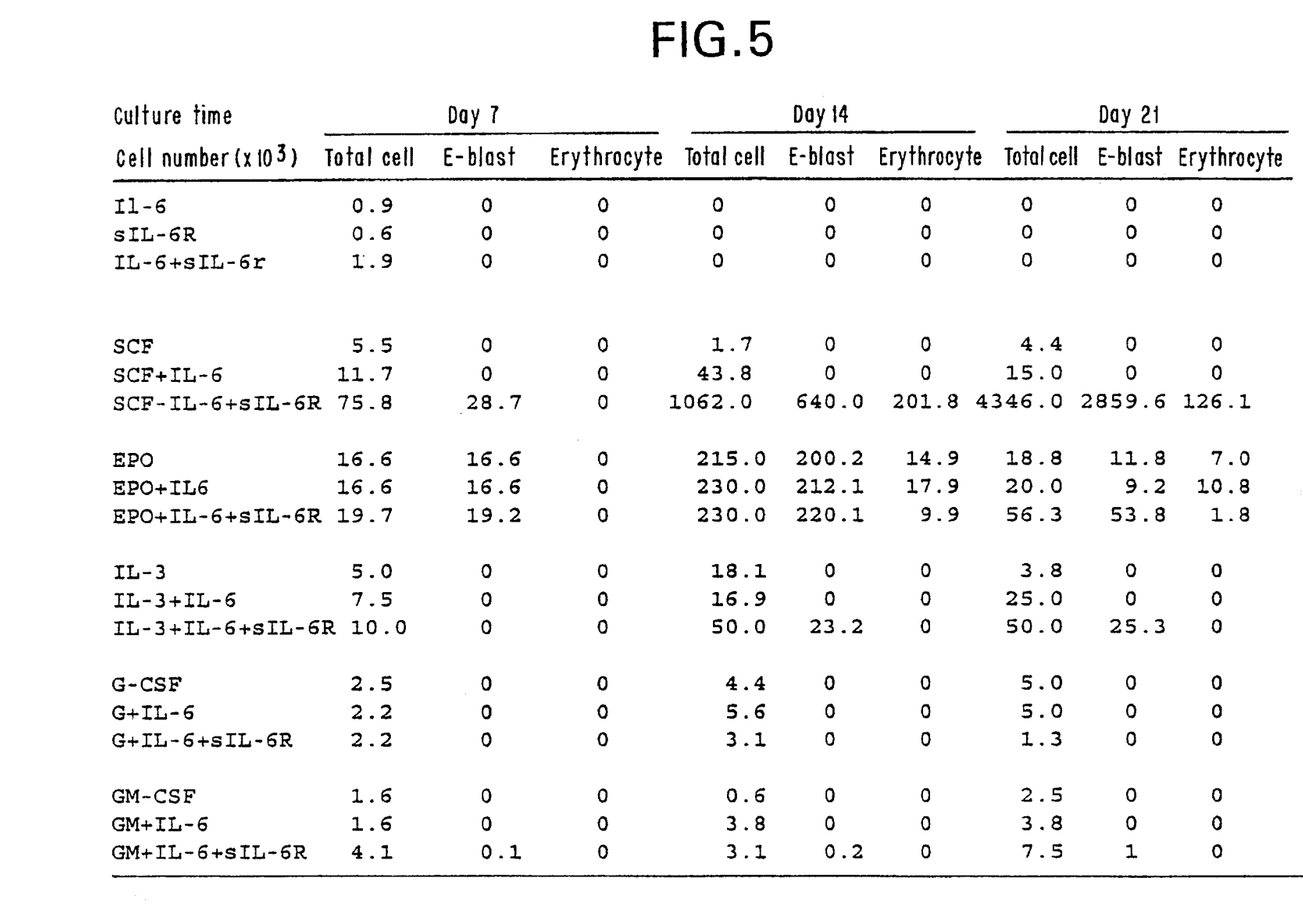
FIG. 5 illustrates the total cell numbers, E-blasts and erythrocytes produced by different combinations of cytokines at 7, 14 and 21 days of culture. IL-3 is interleukin-3, G-CSF is granulocyte colony stimulating factor, and GM-CSF is granulocyte-macrophage colony stimulating factor.

No erythroid cells were detectable in cultures receiving other cytokine combinations, except those combinations which included erythropoietin. In comparison to erythropoietin alone, the total number of erythroid cells produced by the combination of sIL-6R, IL-6 and SCF was about 5-fold at 14 days of culture, and about 115-fold at 21 days of culture (FIG. 5). In comparison to a combination of erythropoietin, sIL-6R and IL-6, the total number of erythroid cells produced by the sIL-6R/IL-6/SCF combination was about 4.1-fold at 14 days of culture, and about 38.3-fold at 21 days of culture. The effect of the sIL-6R/IL-6/SCF combination on the generation of erythroid cells was observed in both serum-containing and serum-free culture of CD34+ bone marrow cells (data not shown).

In the suspension cultures receiving the sIL-6R/IL-6/SCF combination, it was likely that the generation of the large number of erythroid cells resulted from the proliferation, differentiation and maturation of immature erythroid progenitors in the CD34+ cell population. To confirm this possibility, methylcellulose clonal cultures of CD34+ cells were studied. Cultures received either erythropoietin alone, combined erythropoietin/IL-6 or an erythropoietin/sIL-6R/IL-6 combination. Table 1 depicts the results produced from 500 CD34+ cord blood cells cultured for 14 days.

TABLE 1

|  | Erythroid Bursts | Mixed Erythroid Colonies |
| --- | --- | --- |
| EPO | 57.7 ± 14.8 | 0 |
| EPO/IL-6 | 63.0 ± 3.5 | 0 |
| EPO/sIL-6R/IL-6 | 65.0 ± 7.6 | 9 ± 6.1 |

Figure 4E:
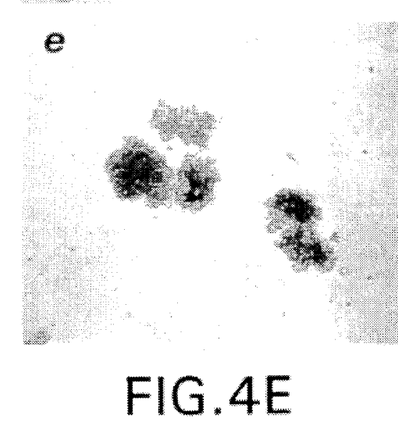
Figure 4F:
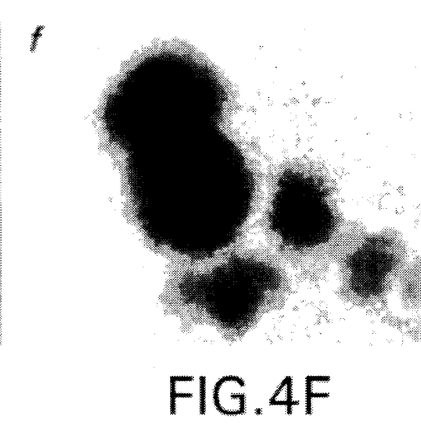

The combination of sIL-6R, IL-6 and SCF, in the absence of erythropoietin, stimulated not only erythroid bursts, but also generated many large mixed erythroid colonies. All of the mixed erythroid colonies contained many mature erythroid cells, including erythrocytes (FIG. 4f and FIG. 4g). The sIL-6R/IL-6/SCF combination produced 27.2±5.8 erythroid bursts and 122.3±21.8 mixed erythroid colonies from the 500 CD34+ cord blood cells. In contrast, neither erythroid bursts nor mixed erythroid colonies were observed in cultures receiving SCF alone or SCF in combination with IL-6. The generation of erythroid bursts and mixed erythroid colonies from both cord blood and bone marrow stem cells using the sIL-6R/IL-6/SCF combination was also confirmed in serum-free cultures (data not shown). When bone marrow mononuclear cells which contain mature erythroid progenitors (i.e., colony forming unit-erythroid) were cultured with the sIL-6R/IL-6/SCF combination, a number of erythroid colonies were observed. These results strongly suggested that the sIL-6R/IL-6/SCF combination can support proliferation, differentiation and terminal maturation not only of immature erythroid progenitors in the CD34+ cell population but also mature erythroid progenitors in bone marrow mononuclear cells.

Figure 6:
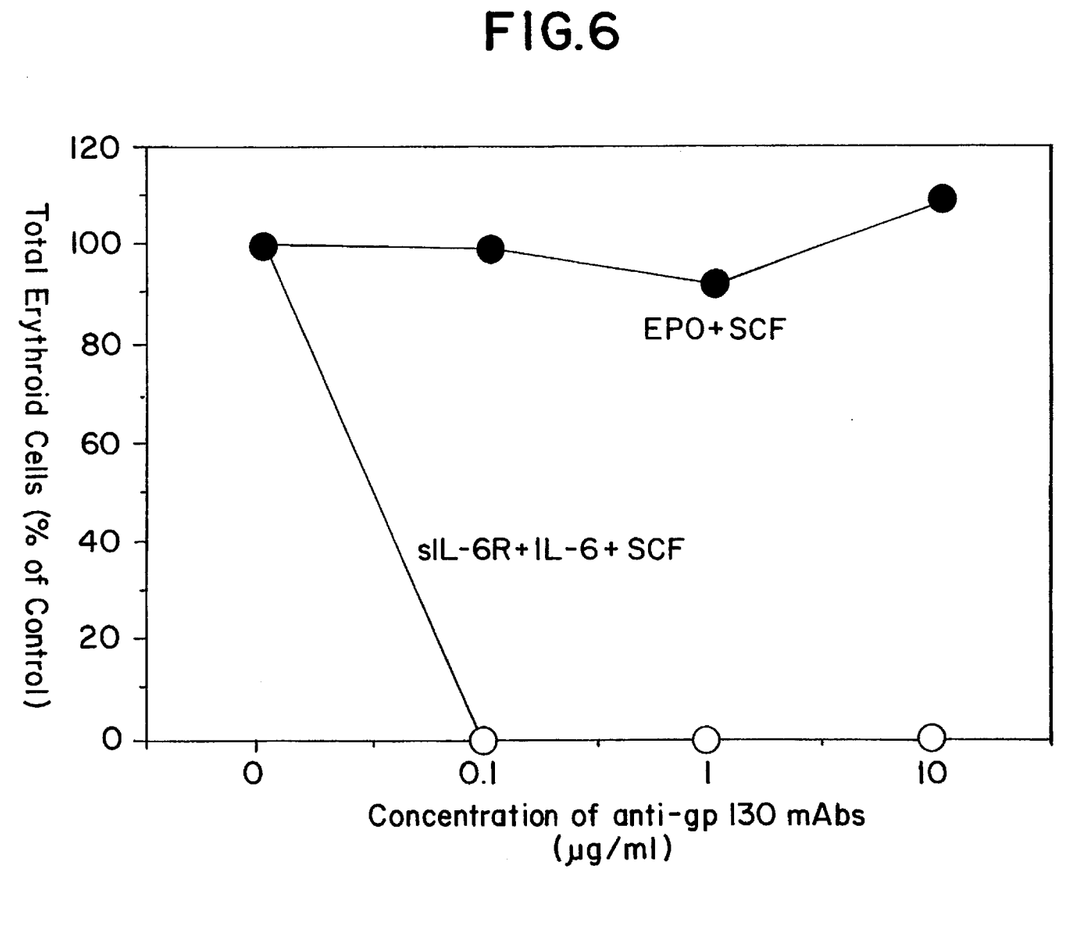
FIG. 6 depicts the effects of anti-gp130 MAbs (μg/ml) on suspension cultures receiving a combination of sIL-6R/IL-6/SCF or EPO/SCF.

To further test the possibility of an alternative pathway for the regulation of erythropoiesis, we examined the effects of different antibodies on cell development. The effects of the following antibodies were studied: anti-gp130 MAbs (GPX7, GPX22 and GPZ35) which block the interaction between sIL-6R/IL-6 complex and cell-surface gp130 (10–11); anti-IL-6R MAb which blocks the interaction between IL-6 and IL-6R (12); and anti-erythropoietin neutralizing antibody which blocks the development of erythroid cells from CD34+ cells. The addition of anti-gp130 MAbs to the suspension culture receiving the sIL-6R/IL-6/SCF combination completely abrogated the production of erythroid cells (FIG. 6). The anti-gp130 antibodies, however, had no effect on the erythropoietin-dependent production of erythroid cells.

Figure 7:
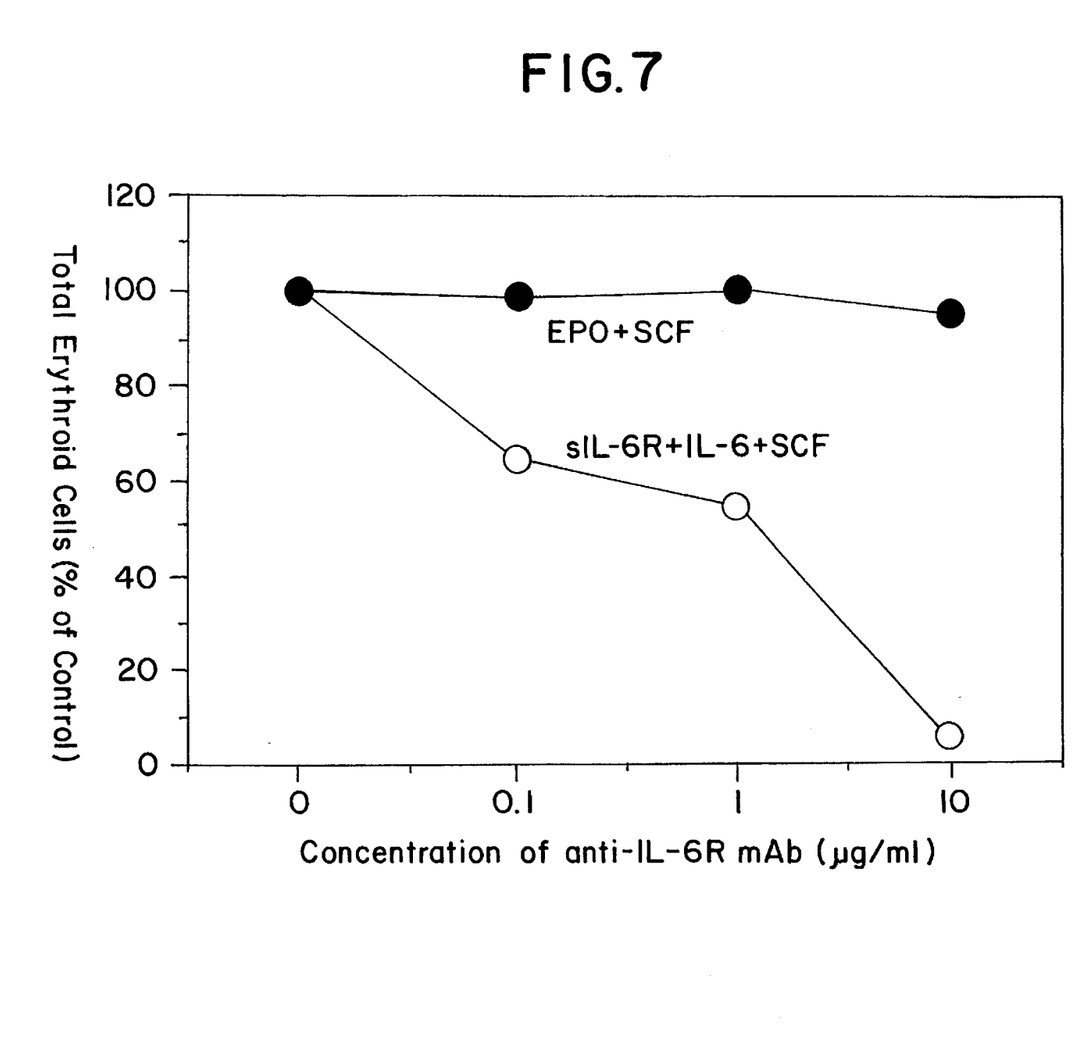
FIG. 7 depicts the effects of an anti-IL-6R MAb (μg/ml) on suspension cultures receiving a combination of sIL-6R/IL-6/SCF or EPO/SCF.
Figure 8:
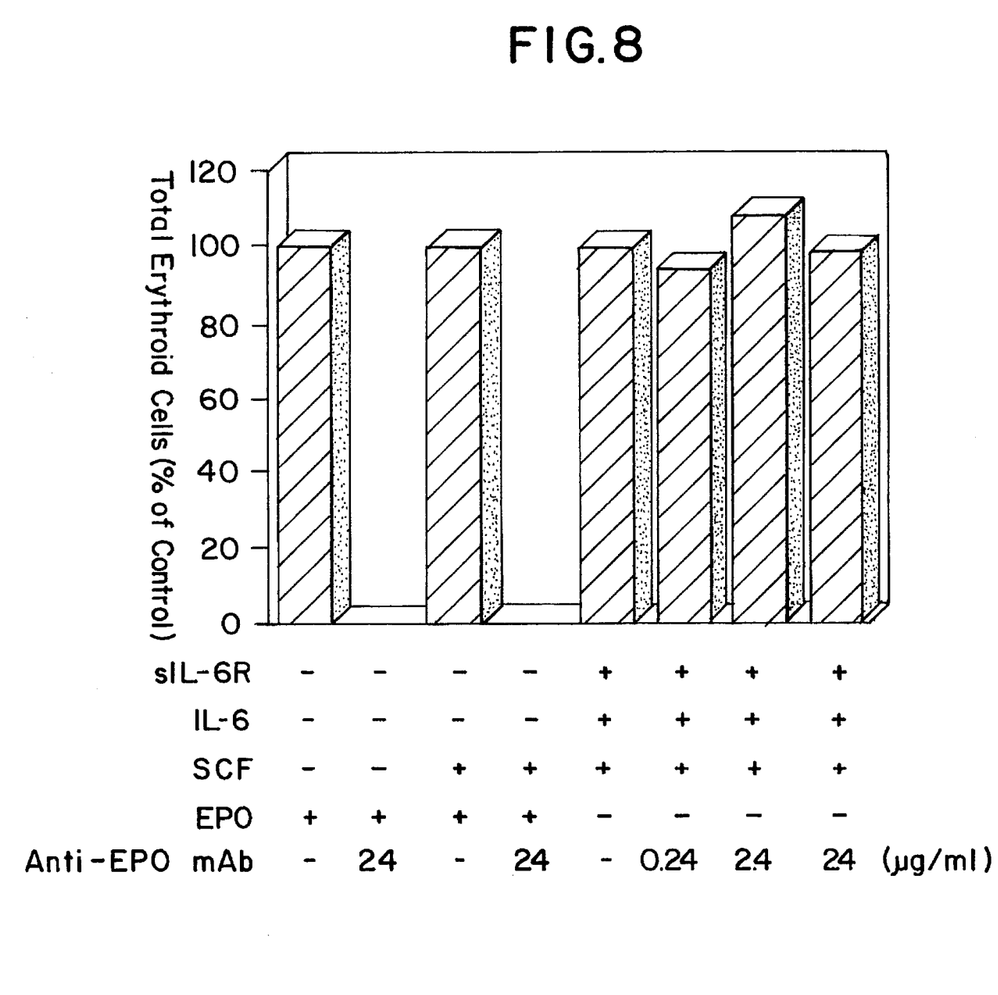
FIG. 8 depicts the effects of an anti-EPO antibody (μg/ml) on suspension cultures receiving EPO, EPO/SCF or a combination of sIL-6R/IL-6/SCF.

The addition of the anti-IL-6R MAb, at a concentration of 10 µg/ml, to cultures receiving the sIL-6R/IL-6/SCF combination resulted in almost complete inhibition of erythroid cell production (FIG. 7). The lower efficiency of the anti-IL-6R MAb may be explained by the excess of sIL-6R which may interfere with the antibody neutralization of the interaction between IL-6 and the cell surface IL-6R. In contrast, although an anti-erythropoietin antibody almost completely inhibited erythropoietin-dependent production of erythroid cells, it failed to affect the generation of erythroid cells by the sIL-6R/IL-6/SCF combination (FIG. 8).

Methylcellulose clonal culture of hematopoietic stem cells also indicated that the anti-gp130 MAbs, but not the anti-erythropoietin antibody, completely blocked the development of both erythroid burst and mixed erythroid colony formation which was otherwise induced by the sIL-6R/IL-6/SCF combination. These results clearly demonstrate that the observed effects of the interleukin-6 ligand and soluble receptor result from the interaction of IL-6 and sIL-6R, and the association of the resulting IL-6/sIL-6R complex with membrane-anchored gp130 on the target progenitor cells. The results also indicated that the generation of erythroid cells from immature erythroid progenitors by gp130 signaling in combination with SCF occurs independently from the presence of erythropoietin.

It has been believed that the proliferation and terminal maturation of erythroid cells are regulated physiologically by erythropoietin receptor signaling. The present invention demonstrates that gp130 signaling combined with SCF will stimulate immature erythroid progenitors, giving rise to erythroblasts and erythrocytes in the absence of erythropoietin. This in turn suggests that erythropoietin receptor signaling is not obligatory for proliferation, differentiation and terminal maturation of normal human erythroid cells. The significant production of erythroid cells by the sIL-6R/IL-6/SCF combination, and the lack of such production by stem cells which did not receive sIL-6R, is reminiscent of previous reports that sIL-6R confers IL-6 responsiveness to cells which lack transmembrane IL-6R but which express gp130. This theory was supported by the immunocytological staining experiments which demonstrated that all CD34+ cells and proliferating cells expressed gp130, but about 90% of the CD34+ cells receiving the sIL-6R/IL-6/SCF combination were negative for IL-6R staining.

It has been reported that the physiological significance of sIL-6R is indicated by its detection in human sera (5). The sIL-6R present in sera is biologically active in terms of its ability to bind IL-6 and eventually to stimulate gp130 (13). A half-maximal effect of the combination of sIL-6R and IL-6 on the generation of erythroid cells from CD34+ cells in vitro was observed at concentrations of 320 ng/ml of sIL-6R and 25 ng/ml of IL-6. This seems likely to be within the physiological range. IL-6 and SCF are also detectable in human sera. Like IL-6, both soluble and membrane-bound forms of SCF are produced by bone marrow stroma cells which may anchor hematopoietic stem cells and immature progenitors and support their proliferation in bone marrow (6,7,14,15). Taken together, the current results indicate that SCF, in combination with gp130 signaling, plays an important role on normal erythropoiesis in vivo.

EXAMPLES

Example 1

Proliferative Activity of sIL-6R and IL-6 on Human Hematopoietic Stem Cells

METHODS. Human umbilical cord blood, obtained according to institutional guidelines, was collected during normal full-term deliveries. Mononuclear cells were separated by Ficoll-Hypaque density gradient centrifugation after depletion of phagocytes with Silica (IBL, Fujioka, Japan). After washing, the mononuclear cells were mixed with magnetic particles bearing anti-CD34 antibody (Dynabeads M-450 CD34; Dynal, Oslo, Norway), with a bead to cell ratio of 1:1. The cell-bead suspension was suspended and incubated at 4° C. for 30 minutes to allow cell binding to the beads. The resulting beads/rosetted cells were collected in a Dynal Magnetic Particle Concentrator. The beads were detached from the positively selected cells by DETACHaBead CD34 (Dynal), according to the manufacturer's instructions, to retrieve the selected CD34+ cells. The purity of the separated CD34+ cells was 85–95% by FACS analysis (Ortho, USA).

Colony efficiency in methylcellulose culture, supplemented with SCF, IL-3, IL-6, erythropoietin and G-CSF, was 45–55%. Purified CD34+ cells were cultured in suspension culture using the techniques previously described (16,17) with the following modifications. Culture medium contained 2000 CD34+ cells, α-medium, 20% fetal bovine serum (FBS; HyClone, UT), 1% crystallized and deionized bovine serum albumin (BSA, Sigma). One milliliter of culture mixture and different combinations of recombinant human sIL-6R, IL-6, and SCF (100 ng/ml) were incubated in 24-well tissue plates (Nunc, Kamstrup, Denmark) at 37° C. with 5% $CO_2$ and 5% $O_2$. Recombinant sIL-6R, IL-6 and SCF were produced and used as previously described. Serum-free suspension cultures consisted of 2% pure BSA (Sigma), 10 µg/ml insulin, 200 µg/ml transferrin, $10^{-5}$M mercaptoethanol (Eastman) and 40 µg/ml low-density lipoprotein (Nakarai Tesque Inc., Tokyo), instead of FBS (19). At weekly intervals, half of the medium was exchanged with fresh medium containing the same set of cytokines. A fraction of the cells was then harvested, washed, counted in a hemocytometer, cytocentrifuged and stained.

RESULTS. The results of the study are presented in FIGS. 1 through 3, as discussed above. FIG. 1 depicts stem cell growth, in serum-containing suspension culture, using varying concentrations of sIL-6R with SCF in the presence (open circles) or absence (filled circles) of IL-6 (50 ng/ml) at 14 days of incubation. FIG. 2 depicts stem cell growth, in serum-containing suspension culture, using varying concentrations of IL-6 with SCF in the presence (open circles) or absence (filled circles) of sIL-6R (1280 ng/ml) at 14 days of incubation. FIG. 3 depicts stem cell growth in serum-containing and serum-free cultures containing either SCF alone, a combination of SCF and IL-6 (50 ng/ml) or a combination of SCF/IL-6 and sIL-6R (1280 ng/ml) at day 7 (open columns), day 14 (oblique columns) and day 21 (filled columns). The results are from three separate experiments. Standard deviations are represented by error bars.

Example 2

Development of Erythroid Cells from Hematopoietic Stem Cells in Culture with Combined Cytokines METHODS. Cytocentrifuge preparations of suspension culture were stained with May-Grunwald-Giemsa at day 7 and day 14 by conventional methods. At day 14, preparations were also immunostained with the alkaline phosphatase anti alkaline phosphatase (APAAP) method using MAbs against antiglycophorin A (Immunotech Co, Marseilles, France) and anti hemoglobin a-chain (COSMO Bio Co., Tokyo, Japan) according to previously described methods (20). Positive cells were stained with reddish granules. Methylcellulose culture was conducted as previously reported (21,22). Culture mixture contained 500 CD34$^+$ cord blood cells, α-medium, 0.9%, 30% FBS, 1% BSA, $5 \times 10^{-5}$M mercaptoethanol, 1280 ng/ml sIL-6R, 80 ng/ml IL-6 and 100 ng/ml SCF. One milliliter of culture mixture was plated in each 35 mm Lux standard nontissue culture dish. Cells were incubated at 37° C. in a humidified atmosphere with 5% $CO_2$ in air.

RESULTS. The results of the study are presented in FIG. 4. Cytocentrifuge preparations of suspension culture stained with May-Grunwald-Giemsa are depicted at day 7 (FIG. 4a) and day 14 (FIG. 4d). Cytocentrifuge preparations of the culture immunostained with antiglycophorin-A MAb or anti hemoglobin-alpha MAb at day 14 are depicted in FIGS. 4b and 4c, respectively. Representative erythroid burst and mixed erythroid colony generated from erythroid progenitor cells in methylcellulose culture with sIL-6R, IL-6 and SCF at day 14 are depicted in FIGS. 4e and 4f, respectively.

Example 3

Antibody Effects on Erythroid Cell Production

METHODS. The following experiment examined the effects of anti-human gp130 MAbs, anti-human IL-6R MAb and anti-human erythropoietin antibody on the generation of erythroid cells. The preparation of anti-human gp130 MAbs (GPX7, GPX22 and GPZ35) has been described previously (9). In brief, mice were immunized with recombinant human soluble gp130, and hybridomas producing the anti-human gp130 MAbs GPX7, GPX22 and GPZ35 were established. The three antibodies recognize different epitopes on gp130 and inhibit IL-6-mediated biological response through the inhibition of the IL-6-induced association of gp130 with IL-6 receptors (9,11). Anti-human IL-6R (PM1) MAb was prepared (12). PM1 inhibits IL-6-mediated biological response through inhibition of the binding of IL-6 to the IL-6 receptors. Rabbit anti-human erythropoietin antibody (IgG K-5) was provided by Kirin Co., Japan. Anti-erythropoietin antibody (24 mg/ml) neutralizes 2U/ml of erythropoietin (23).

As illustrated in FIG. 6, human cord blood stem cells (2000 CD34$^+$cells) were supplemented with either a combination of sIL-6R/IL-6/SCF (open circles) at the predetermined optimal concentrations, or a combination of erythropoietin (2 U/ml) and SCF (100 ng/ml) (filled circles). Cultures were observed with and without the addition of mouse anti-human gp130 MAbs (FIG. 6), mouse anti-human IL-6R MAb (PM1) (FIG. 7) or rabbit anti-human erythropoietin antibody (FIG. 8) in serum-containing suspension culture, made as described in Example 1. Graded concentrations of the antibodies were added at the beginning of the culture. The wells to which no antibodies were added were used as controls. After culturing for 14 days, the cells were harvested, counted and cytocentrifuged. Total erythroid cells (including erythroblasts, normoblasts and erythrocytes) were calculated based on the total cell number and the proportion of the erythroid cells determined on the cytospin slides. The resulting data represent the ratio of the erythroid cells in each well treated with antibodies to the erythroid cells in each control well, and are expressed as a percent (%) of control.

REFERENCES

1. Krantz, S .B., *Blood*, 77: 419–434 (1991).
2. Yu, H., Bauer, B., Lipke, G. K., Phillips, R. L. & Van Zant, G., *Blood*, 81:373–384 (1993).
3. Koury, M. J. & Bondurant, M. C., *Science*, 248:378–381 (1990).
4. Liboi, E., Carroll, M., D'Andrea, A. D. & Mathey-Prevot, B., *Proc. Natl. Acad. Sci., USA*, 90:11351–11355 (1993).
5. Honda, M., Tamamoto, S., Cheng, M., Yasukawa, K., Suzuki, H., Saito, T., Osugi, Y., Tokunaga, T. & Kishimoto, T., *J. Immunol.*, 148:2175–2180 (1992).
6. Honda, M., Kitamura, K., Mizutani, Y., Oishi, M., Arai, M., Okura, T., Igarahi, K., Yasukawa, K., Hirano, T., Kishimoto, T., Mitsuyasu, R., Chermann, J-C. & Tokunaga, T., *J. Immunol.*, 145:4059–4064 (1990).
7. Langley, K. E., Bennett, L. G., Wypych, J., Yancik, S. A., Liu, X. D., Westcott, K. R., Chang, D. G., Smith, K. A. & Zsebo, K. M., *Blood*, 81:656–660 (1993).
8. Taga, T., Hibi, M., Hirata, Y., Yamasaki, K., Yasukawa, K., Matsuda, T., Hirano, T. & Kishimoto, T., *Cell*, 58:573–581 (1989).
9. Taga, T., Narazaki, M., Yasukawa, K., Satio, T., Miki, D., Hamaguchi, M., Davis, S., Shioyab, M., Yancopoulos, G. D. & Kishimoto, T., *Proc. Natl. Acad. Sci., USA*, 89:10998–11001 (1992).
10. Yin, T., Taga, T., Tsang, M. L-S., Yasukawa, K., Kishimoto, T. & Yang, Y-C., *J. Immunol.*, 151:2555–2561 (1993).
11. Saito, T., Taga, T., Miki, D., Futatsugi, K., Yawata, H., Kishimoto, T. & Yasukawa, K., *J. Immunol. Methods*, 163:217–233 (1993).
12. Hirata, Y., Taga, T., Hibi, M., Nakano, N., Hirano, T. & Kishimoto, T., *J. Immunol.*, 143:2900–2906 (1989).
13. Suzuki, H., Yasukawa, K., Saito, T., Narazaki, M., Hasegawa, A., Taga, T. & Kishimoto, T., *Eur. J. Immunol.*, 23:1078–1082 (1993).
14. Zsebo, K. M., Williams, D. A., Geissler, E. N., Broudy, V. C., Martin, F. H., Atkins, H. L., Hsu, R-Y., Birkett, N. C., Okino, K. H., Murdock, D. C., Jacobsen, F. W., Langley, K. E., Smith, K. A., Takeishi, T., Cattanach, B. M., Galli, S. J. & Suggs, S. V., *Cell*, 63:213–224 (1990).
15. Flanagan, J. G. & Leder, P., *Cell*, 63:185–194 (1990).
16. Iscove, N. N., Shaw, A. R. & Keller G. J., *Immunol.*, 142:2332–2337 (1989).
17. Mayani, H. & Lansdrop, P., *Blood*, 83:2410–2417 (1994).
18. Yasukawa, K., Satio, T., Fukunaga, T., Sekimori, Y., Koishihara, Y., Fukui, H., Ohsugi, Y., Matsuda, T., Yawata, H., Hirano, T., Taga, T. & Kishimoto, T., *J. Biochem.*, 108:673–676 (1990).
19. Koike, K., Nakahata, T., Takagi, M., Kobayashi, T., Ishiguro, A., Tsuji, K., Naganuma, K., Okano, A., Akiyama, Y. & Akabane, T., *J. Exp. Med.*, 168:879–890 (1988).
20. Okumura, N., Tsuji, K. & Nakahata, T., *Blood*, 80:642–650 (1992).
21. Nakahata, T. & Ogawa, M., *J. Clin. Invest.*, 70:1324–1328 (1982).

22. Imai, T. , Koike, K., Kubo, T., Kikuchi, T., Amano, Y., Takagi, M., Okumura, N & Nakahata, T., *Blood*, 78:1969–1974 (1991) .

23. Nishi, N., Nakahata, T., Koike, K. , Takagi, M., Naganuma, K. & Akabane, T., *Blood*, 76:1330–1335 (1990).

What is claimed is:

1. A method of producing erythroid cells in vitro. comprising: culturing hematopoietic cells in a culture medium comprising stem cell factor, an interleukin-6 and soluble interleukin-6 receptor to induce proliferation and differentiation of said hematopoietic cells and thereby producing erythroid cell wherein said stem cell factor, interleukin-6 and soluble interleukin-6 receptor is in an amount effective to induce proliferation and differentiation of said hematopoietic cells.

2. The method according to claim 1, wherein said soluble interleukin-6 receptor is used at a concentration of at least 80 ng/ml to 1280 ng/ml.

3. The method according to claim 2, wherein said interleukin-6 is used at a concentration of at least 50 ng/ml to 100 ng/ml.

4. A method for producing erythroid cells for hematopoietic cell transplantation in a subject, comprising the steps of:

a) removing hematopoietic progenitor cells from the subject;

b) contacting said hematopoietic cells in a culture medium comprising stem cell factor, interleukin-6 and soluble interleukin-6 receptor, wherein said stem cell factor, interleukin-6 and soluble interleukin-6 receptor are derived from the same mammalian species as that of said subject;

c) culturing said cells ib vitro, to produce a cellular preparation; wherein said culturing induces proliferation and differentiation of said hematopoietic cells and thereby produces erythroid cell; and d) administering said cellular preparation to the subject.

5. The method according to claim 4, wherein said soluble interleukin-6 receptor is used at a concentration of at least 80 ng/ml to 1280 ng/ml.

6. The method according to claim 5, wherein said interleukin-6 is used at a concentration of at least 50 ng/ml to 100 ng/ml.

* * * * *